United States Patent [19]

Tinti et al.

[11] Patent Number: 4,567,200

[45] Date of Patent: Jan. 28, 1986

[54] ESTERS OF MERCAPTO ACYL-CARNITINES AND PHARMACEUTICAL COMPOSITIONS CONTAINING SAME

[75] Inventors: Maria O. Tinti; Emma Quaresima; Carlo Bagolini; Paolo deWitt, all of Rome, Italy

[73] Assignee: Sigma-Tau Industrie Farmaceutiche Riunite S.p.A., Rome, Italy

[21] Appl. No.: 358,502

[22] Filed: Mar. 15, 1982

[30] Foreign Application Priority Data

Mar. 31, 1981 [IT] Italy ............................... 48166 A/81

[51] Int. Cl.$^4$ ..................... A61K 31/22; A61K 31/23; C07C 149/243
[52] U.S. Cl. ................................ 514/547; 260/402.5; 260/390; 424/DIG. 13; 560/147; 560/125; 560/16; 560/15; 514/529; 556/134
[58] Field of Search ............................... 560/147, 125; 260/402.5; 424/311, 312, DIG. 13, 305; 514/547, 529

[56] References Cited

FOREIGN PATENT DOCUMENTS 46-2247  1/1971  Japan ................................ 560/253

*Primary Examiner*—Vivian Garner
*Attorney, Agent, or Firm*—Ladas & Parry

[57] ABSTRACT

A novel class of esters of mercapto acyl-carnitines is disclosed, wherein the mercapto acyl radical is the radical of saturated mercapto acids having from 2 to 10 carbon atoms. These esters of mercapto acyl-carnitines are prepared e.g. by first preparing the corresponding ester of halogen acyl-carnitine and then substituting therein, by nucleophylic substitution, the —SH group for the halogen atom.

These esters of mercapto acyl-carnitines are useful therapeutic agents, e.g. for the treatment of intoxications and burns, and as mucolytic agents.

11 Claims, No Drawings

ESTERS OF MERCAPTO ACYL-CARNITINES AND PHARMACEUTICAL COMPOSITIONS CONTAINING SAME

The present invention relates to a novel class of carnitine derivatives and, more particularly, it relates to esters of mercapto acyl-carnitines wherein the mercapto acyl radical is the radical of saturated mercapto acids having from 2 to 10 carbon atoms.

The present invention also relates to the processes for the preparation of such esters of mercapto acyl-carnitines and to pharmaceutical compositions containing same.

More specifically, the present invention relates to compounds having general formula:

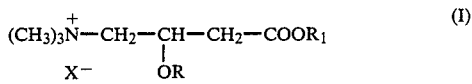

wherein:
$X^-$ is a pharmacologically acceptable halogenide ion, preferably the chloride ion,
R is the mercapto acyl radical of a saturated mercapto acid having from 2 to 10 carbon atoms, and
$R_1$ is a straight or branched alkyl radical having from 1 to 5 carbon atoms.

This mercapto acyl radical is preferably selected from the group consisting of: mercapto acetyl, 2-mercapto propionyl, 3-mercapto propionyl, 2-mercapto butyryl, 4-mercapto butyryl and 5-mercapto valeryl.

The alkyl radical is preferably selected from the group consisting of: methyl, ethyl, propyl, isopropyl, butyl and isobutyl.

Mercapto acyl-carnitine esters preferred according to this invention are:
mercapto acetyl carnitine isopropyl ester
2-mercapto propionyl carnitine isobutyl ester
3-mercapto propionyl carnitine ethyl ester
2-mercapto butyryl carnitine isobutyl ester
4-mercapto butyryl carnitine isobutyl ester, and
5-mercapto valeryl carnitine methyl ester.

A process for preparing the mercapto acyl-carnitine esters of formula (I) comprises the steps of:
(a) reacting an ester of carnitine hydrochloride with a halogen acyl chloride in the presence of an organic solvent inert towards the reaction at a temperature comprised between about 30° and about 60° C., thus obtaining the corresponding ester of halogen acyl-carnitine; and
(b) reacting at room temperature the ester of halogen acyl-carnitine of step (a) with a compound selected from the class of alkali metal sulfides and acid sulfides, keeping the pH of the resulting reaction mixture substantially at neutrality by adding an inorganic acid selected between hydrochloric acid and sulfuric acid, thus obtaining the ester of mercapto acyl-carnitine.

In step (a) the organic solvent is preferably selected among trifluoro acetic acid, methylene chloride and chloroform.

In step (b) the compound selected from the class of the alkali metal sulfides and acid sulfides is preferably NaHS.

A further process for preparing the mercapto acyl-carnitine esters of general formula (I) comprises the following steps:
(a') reacting an ester of carnitine hydrochloride with a mercapto acyl chloride wherein the SH group is protected with a protective group selected between trityl and p-substituted benzyl, thus obtaining the corresponding S-protected mercapto acyl-carnitine ester; and
(b') removing by known per sè techniques the protective group of the S-protected mercapto acyl-carnitine ester of step (a').

In step (b'), when the protective group is either trityl or p-methoxybenzyl, this protective group is removed by acid hydrolysis. When the protective group is p-nitrobenzyl, this group is removed by
(1) converting the nitro group into amino group by hydrogenolysis, e.g. hydrogenating with a Parr hydrogenator at 30–50 psi in the presence of a palladium on carbon catalyst;
(2) treating the S-para amino benzyl derivative thus obtained with the Hopkins reagent and isolating the resulting mercapto acyl-carnitine mercury salt; and
(3) treating the mercury salt thus obtained with $H_2S$ and isolating the resulting mercapto acyl-carnitine.

The following non-limiting example illustrates the preparation and the chemico-physical characteristics of a compound according to the present invention.

EXAMPLE

Preparation of mercapto acetyl carnitine hydrochloride isopropyl-ester (a') Preparation of S-p-nitrobenzyl mercapto acetyl carnitine hydrochloride isopropyl ester A suspension of S-(p-nitrobenzyl) mercapto acetic acid (8.4 grams; 0.04 moles) and oxalyl chloride (10.5 ml; 0.12 moles) was reacted for 4 hours at room temperature (over the time a solution formed). The excess of oxalyl chloride was evaporated and the residue was washed with small volumes of anhydrous ethyl ether (3 times × 10 ml.). The S-p-nitrobenzyl mercapto acetyl thus obtained was used as such in the subsequent reaction.

A substantially homogeneous mixture of carnitine hydrochloride isopropyl ester (2.4 grams; 0.01 moles) and the foregoing acid chloride (7 grams; 0.03 moles) was kept to react at the temperature of 45° C., under magnetic stirring, for 1 day. The end of the reaction was checked by TLC. The reaction mixture was diluted with acetonitrile (30 ml.) and the resulting solution was poured in 200 ml. of ethyl ether. The raw precipitate was crystallized from acetonitrile-ethyl ether.

Anal. ($C_{19}H_{29}ClN_2O_6S$) C, H, Cl, N, S.

NMR ($D_2O$) δ = 1.37 (6H, d 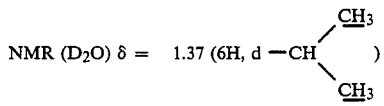 )

2.87–3.07 (2H, m, $-CH_2COO-$);

3.47 (11H, s, $-\overset{+}{N}-(CH_3)_3$ and $-SCH_2-$);

3.90–4.13 (4H, m, $\overset{+}{\underset{/}{\overset{\backslash}{N}}}-CH_2-$ and $-CH_2Ar$);

4.73–5.13 (1H, m, 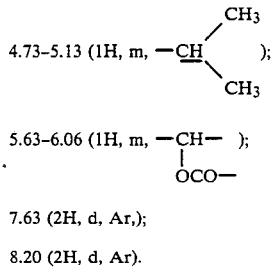);

5.63–6.06 (1H, m, —CH— );
                      |
                     OCO—

7.63 (2H, d, Ar,);

8.20 (2H, d, Ar).

(b') Removal of the protective group 1.1 grams of 10% Pd/C were added to a solution of S-p-nitrobenzyl mercapto acetyl carnitine hydrochloride isopropyl ester (2.2 grams; 0.0005 moles) in isopropanol (70 ml.). The resulting mixture was hydrogenated at 40 psi (with a Parr hydrogenator) under stirring at room temperature for 18 hours. Subsequently, the reaction mixture was filtered on celite and to the filtrate Et₂O was added until complete precipitation of a product which was shown to be S-p-aminobenzyl mercapto acetyl carnitine hydrochloride isopropyl ester.

NMR (D₂O); the δ range of the protons of the aromatic group

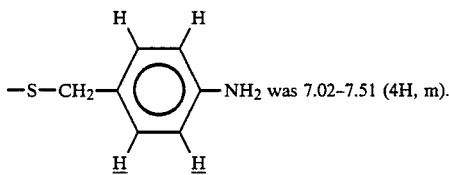 was 7.02–7.51 (4H, m).

Subsequently, the S-p-aminobenzyl derivative (1.13 grams; 0.003 moles) was dissolved in EtOH (100 ml.) and 1N HCl (50 ml.). 75 m. of the Hopkins reagent (J. Org. Chem. 1972, 37/22 3551): 10% HgSO₄ in 5% H₂SO₄ were added to this solution.

After some minutes the precipitation of a yellowish solid began at room temperature and under magnetic stirring. After 1 hour, this solid precipitate was filtered off from the reaction mixture and the precipitate was washed with H₂O (20 ml.) and Et₂OH (20 ml.).

This solid product (1.86 grams) was suspended in H₂O (50 ml.) and the resulting suspension was saturated with H₂S; after some minutes HgS precipitated, which was filtered off from the reaction mixture. The remaining solution was evaporated under vacuum. The residue, taken up with the amount of H₂O sufficient to dissolve it, was percolated through IR 45 resin (activated in the OH⁻ form). After acidifying to pH2–3, the eluate was lyophilized. The product thus obtained was crystallized from isopropanol-Et₂O and was shown to be the title compound.

Anal. (C₁₂H₂₄ClNO₄S) C, H, Cl, S.

NMR (D₂O) δ = 1.30 (6H, d, 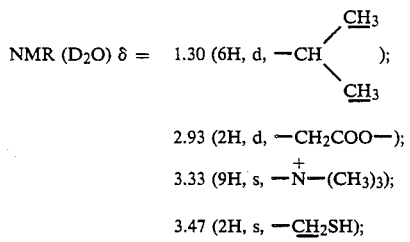);

2.93 (2H, d, —CH₂COO—);

3.33 (9H, s, —N⁺—(CH₃)₃);

3.47 (2H, s, —CH₂SH);

3.74–4.00 (2H, m, —CH₂N⁺—);

4.73–5.27 (1H, m, 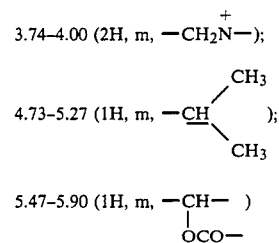);

5.47–5.90 (1H, m, —CH— )
                      |
                     OCO—

It has been found that the mercapto acyl-carnitine esters of formula (I) are useful therapeutic agents for the treatment of intoxications, for the treatment of burns and the diseases of the epithelia (and in general whenever it is important to restore to normal the metabolic cellular equilibrium unbalanced by exogenous and endogenous factors) and as mucolytic agents.

It is known that lack of sulphydryl groups SH available for the metabolism requirements, as well as the inability of the organism to utilize such groups in specific pathological situations, constitute the primary factor of anatomical and functional alterations of some body tissues. Indeed, the activity of most of the enzymes present in the cells of vital organs, such as liver, is related to the presence of SH groups in their molecules as well as to the activity of SH groups at the membrane level.

It is also known that the organism, when because of various reasons is unable to utilize the sulphydryl groups indispensable for the cellular metabolism to take place regularly, can utilize the sulphydryl groups that it derives from the administration of compounds containing such groups.

It has been difficult up to now to have available compounds able to cross the biologic membranes and free the SH groups in order to re-constitute the cellular membranes and restore the enzyme activity.

It has now been found that the compounds of the present invention possess a remarkable ability to cross the biologic membranes and particularly the mitocondrial membranes.

Moreover, the mercapto acyl-carnitines provide, in addition to the SH groups, the energy related to the acyl groups (typically, acetyl) which is needed for essential metabolic processes to take place.

The characteristics of pharmacological activity of the compounds of general formula (I) are hereinbelow illustrated.

Acute toxicity

The acute toxicity of the compounds of general formula ( I) has been studied in the mouse with the Weil method (Weil C.S., Biometr. J. 8, 249, 1952).

The LD50 values of some compounds illustrated in Table I, indicate that the compounds are remarkably well tolerated.

TABLE I

LD50, mg Kg⁻¹, ep in mice of some mercapto acyl-carnitine esters of general formula (I).
Weil's method (N = 5, K = 4)
Cl = hydro-chloride.

| Compounds | DL50 | Fiducial limits |
|---|---|---|
| mercapto acetyl carnitine Cl isopropyl ester | 250 | 215–285 |
| 2-mercapto propionyl carnitine Cl isobutyl ester | 274 | 239–309 |

TABLE I-continued

LD50, mg Kg$^{-1}$, ep in mice of some mercapto acyl-carnitine esters of general formula (I).
Weil's method (N = 5, K = 4)
Cl = hydro-chloride.

| Compounds | DL50 | Fiducial limits |
|---|---|---|
| 3-mercapto propionyl carnitine Cl ethyl ester | 228 | 183–273 |
| 2-mercapto butyryl carnitine Cl isobutyl ester | 236 | 195–277 |
| 4-mercapto butyryl carnitine Cl isobutyl ester | 231 | 179–283 |
| 5-mercapto valeryl carnitine Cl methyl ester | 219 | 176–262 |

Protection against X-ray exposure

The effect of the compounds of formula (I) towards the damages provoked by X-ray exposure was studied.

The experiment animals, Albino Wister rats, treated with the compounds under examination (20–25 mg Kg$^{-1}$ 1 hour before irradiation and 10 mg Kg$^{-1}$ per day in the subsequent 20 days) were irradiated and checked over a time period to detect the onset of toxic effects and the time of survival with respect to the control group.

In table II, the percentage of survival at the 10th, 15th and 20th day from irradiation are reported.

TABLE II

Protective effect of some mercapto acyl-carnitine esters of general formula (I) towards the damage provoked by irradiation in rats. Percentage of surviving animals at various days from irradiation
car. = carnitine; es. = ester

| Compounds | Days of survival | | |
|---|---|---|---|
| | 10 | 15 | 20 |
| Control | 85 | 20 | 10 |
| mercapto acetyl car. Cl isopropyl es. | 80 | 55 | 30 |
| 2-mercapto propionyl car. Cl isobutyl es. | 85 | 70 | 45 |
| 3-mercapto propionyl car. Cl ethyl es. | 90 | 85 | 60 |
| 2-mercapto butyryl car. Cl isobutyl es. | 95 | 65 | 50 |
| 4-mercapto butyryl car. Cl isobutyl es. | 100 | 75 | 55 |
| 5-mercapto valeryl car. Cl methyl es. | 85 | 60 | 40 |

Cutaneous regeneration

The ability of the compounds of formula (I) to speed up the cutaneous regeneration from burns has been tested in rabbits.

A 4 cm$^2$ cutaneous area of the average-top zone of the test animal back was burned.

The compounds were orally administered in aqueous solution at the dose of 25 mg Kg$^{-1}$ once a day for seven days. The area of cutaneous regeneration, i.e., the area of the newly formed tissue was then measured (Table III).

TABLE III

Effect of compounds of formula (I) on cutaneous regeneration. Percentage of regenerated tissue at the 4th and 8th day from treatment.
car. = carnitine; es. = ester

| Compounds | Days | |
|---|---|---|
| | 4th day | 8th day |
| Control | 20 | 55 |
| mercapto acetyl car. Cl isopropyl es. | 30 | 70 |
| 2-mercapto propionyl car. Cl isobutyl es. | 25 | 65 |
| 3-mercapto propionyl car. Cl ethyl es. | 40 | 100 |
| 2-mercapto butyryl car. Cl isobutyl es. | 35 | 70 |
| 4-mercapto butyryl car. Cl isobutyl es. | 25 | 75 |
| 5-mercapto valeryl car. Cl methyl es. | 45 | 100 |

The expectorant and mucolytic activities of the compounds of formula (I) were determined.

Expectorant activity

The tests were carried out on male rabbits, weighing 2–3 Kg, anesthetized with ethyl urethane, by following the method disclosed by Perry et al. (J. Pharm. Exp. Ther. 73, 65, 1941).

The anesthetized animals, strapped head downward to an operating table at an inclination of 60°, had a cannula inserted in their trachea. Each cannula was connected to a feeding device which delivered a steady flow-rate of pre-heated air (36°–38° C.) at constant humidity (80%). At the lower end of each cannula, a graduated cylinder was fitted, wherein the bronchial secretion was collected. All of the animals breathed spontaneously and consequently they self-regulated the air intake suitable for normal respiration. After an hour following cannula insertion, the animals were administered orally (by stomach tube) the compounds of general formula (I) dissolved in distilled water at the doses indicated in Table IV. Each dose of drug was administered to 5 animals. The control animals (8) were given water only. The amount of secretion was determined after 1, 2 and 4 hours from administration. The results, summarized in Table IV, show that the compounds of general formula (I) do not exert expectorant activity.

Mucolytic activity

The tests were carried out in vitro by using the method disclosed by Morandini et al. (Lotta contro la tuberculosi 47, n. 4, 1977). A thromboelastograph was used to follow the variations induced by the compounds of general formula (I) and acetylcysteine on the rheological properties of human sputum. The results thereof, summarized in Table V, show that the test compounds bring about a greater decrease of human sputum density than that induced by acetylcysteine.

TABLE IV

Effects of compounds of general formula (I) on bronchial secretion

| Number of Animals | Compounds | Percentage variations ± s.e. of bronchial secretion versus values at the following intervals after administration | | |
|---|---|---|---|---|
| | | 1 hour | 2 hours | 4 hours |
| 8 | Controls | +0.6 | +1.2 | +2.4 |
| 5 | mercapto acetyl carnitine Cl isopropyl ester 15 mg orally | +0.5 | +0.7 | +2.1 |
| 5 | 2-mercapto propionyl carnitine Cl isobutyl ester 15 mg orally | −0.1 | −0.1 | +0.5 |
| 5 | 3-mercapto propionyl carnitine Cl ethyl ester 20 mg orally | +0.6 | +0.8 | +1.0 |
| 5 | 2-mercapto butyryl carnitine Cl isobutyl ester 20 mg orally | −0.2 | −0.4 | +0.2 |
| 5 | 4-mercapto butyryl carnitine Cl isobutyl ester 25 mg orally | +0.5 | +0.9 | +2.1 |
| 5 | 5-mercapto valeryl carnitine Cl methyl ester 20 mg orally | +0.3 | +0.5 | +1.0 |

TABLE V

Mucolytic activity in vitro of compounds of general formula (I) and acetylcysteine; modifications of human sputum density. Car. = carnitine

| Compounds | Percentage drop ± s.e. of the tracing versus maximum peak (*) after addition of 1 ml of a 10% solution of the test compounds at the dilutions indicated | |
|---|---|---|
|  | 1/30 | 1/60 |
| mercapto acetyl car. Cl isopropyl ester | 82.5 ± 5 | 44.3 ± 3 |
| 2-mercapto propionyl car. Cl isobutyl ester | 80.4 ± 7 | 42.8 ± 4 |
| 3-mercapto propionyl car. Cl ethyl ester | 79.8 ± 4 | 39.5 ± 5 |
| 2-mercapto butyryl car. Cl isobutyl ester | 95.9 ± 5 | 51.2 ± 3 |
| 5-mercapto valeryl car. Cl methyl ester | 90.2 ± 6 | 48.4 ± 4 |
| Acetylcysteine | 75.6 ± 7 | 23.8 ± 5 |

(*) Mucolytic activity index

Effect on ciliary activity

The ability of the compounds of formula (I) to affect the ciliary motility was studied by observing with the microscope the ciliary movement of rat trachea rings soaked in solutions of the test compounds.

By this technique it is possible to study, with relation to compound concentration and contact time, the ciliary movement block provoked by the tests compounds, which is related to mucus clearance from ciliary epithelium.

Substances to be used in the form of solutions must allow the foregoing block not to take place in less than fifteen minutes from contact.

2% aqueous solutions of the compounds of formula (I) provoked the ciliary movement block to take place in 18-20 minutes.

As experimentally shown, the compounds of this invention significantly modify the rheological properties of sputum. On perusal of the obtained results a decrease in sputum density at the larger doses (or lower dilutions) and at the smaller doses (or higher dilutions) constantly higher than that provoked by acetylcysteine, is detected. On the other hand no one of the compounds increases bronchial secretion nor is able to block the ciliary movement of the epithelium of trachea ring preparations in time intervals shorter than those permitted.

The compounds of the present invention are therapeutically useful for the treatment of burns and the diseases of epithelia, for the treatment of the diseases of the respiratory tract and generally whenever it is important to restore to normal the metabolic cellular equilibrium of epithelia unbalanced by exogenous and endogenous factors. The patients in need thereof will be orally or parenterally administered a therapeutically effective amount of a mercapto acyl-carnitine ester of general formula (I).

The dose of mercapto acyl-carnitine ester of general formula (I) orally or parenterally administered will be generally comprised between about 2 and about 20 mg/Kg of body weight/day, although larger or smaller doses can be administered by the attending physician having regard to the age, weight and general conditions of the patient, utilizing sound professional judgement.

In practice, the mercapto acyl-carnitine esters are orally or parenterally administered in any of the usual pharmaceutical forms comprising the usual excipients, sweeteners, etc., which are prepared by conventional procedures well-known to those persons skilled in pharmaceutical technology. These forms include solid and liquid oral unit dosage forms such as tablets, capsules, solutions, syrups and the like as well as injectable forms, such as sterile solutions for ampoules and phials.

The pharmaceutical composition can be in unit dosage form comprising from about 25 to about 1000 mg of a mercapto acyl carnitine of formula I.

What is claimed is:

1. Mercapto acyl carnitine esters of the general formula

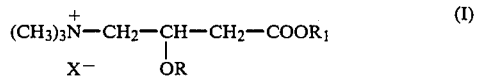

wherein:

$X^-$ is a pharmacologically acceptable halogenide ion;

R is the mercapto acyl radical of a mercapto alkanoic acid having from 2 to 10 carbon atoms; and $R_1$ is a straight or branched alkyl radical having from 1 to 5 carbon atoms.

2. The mercapto acyl-carnitine ester of claim 1, wherein:

$X^-$ is the chloride ion;

R is selected from the group consisting of mercapto acetyl, 2-mercapto propionyl, 3-mercapto propionyl, 2-mercapto butyryl, 4-mercapto butyryl and 5-mercapto valeryl; and $R_1$ is selected from the group consisting of methyl, ethyl, propyl, isopropyl, butyl and isobutyl.

3. As mercapto acyl-carnitine ester of claim 1, mercapto acetyl-carnitine hydrochloride isopropyl ester.

4. As mercapto acyl-carnitine ester of claim 1, 2-mercapto propionyl carnitine hydrochloride isobutyl ester.

5. As mercapto acyl-carnitine ester of claim 1, 3-mercapto propionyl carnitine hydrochloride ethyl ester.

6. As mercapto acyl-carnitine ester of claim 1, 2-mercapto butyryl carnitine hydrochloride isobutyl ester.

7. As mercapto acyl-carnitine ester of claim 1, 4-mercapto butyryl carnitine hydrochloride isobutyl ester.

8. As mercapto acyl-carnitine ester of claim 1, 5-mercapto valeryl carnitine hydrochloride methyl ester.

9. An orally or parenterally administrable pharmaceutical composition for treating burns and as a mucolytic agent which comprises:

(a) a therapeutically effective amount of a mercaptoacyl carnitine ester of general formula (I)

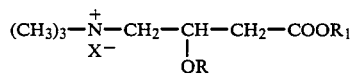

wherein:

$X^-$ is a pharmacologically acceptable halogenide ion,

R is the mercapto acyl radical of a mercapto alkanoic acid having from 2 to 10 carbon atoms; and $R_1$ is a straight or branched alkyl radical having from 1 to 5 carbon atoms, and (b) a pharmaceutically acceptable excipient.

10. The pharmaceutical composition of claim 9 in unit dosage form comprising from about 25 to about 1000 mg of a mercapto acyl-carnitine ester of formula (I).

11. A composition according to claim 9, wherein $X^-$ is chloride.